US006410493B1

(12) United States Patent
Garnier

(10) Patent No.: US 6,410,493 B1
(45) Date of Patent: *Jun. 25, 2002

(54) CONDITIONING AND DETERGENT COMPOSITION COMPRISING AN ANIONIC SURFACTANT, A SILICONE, AND A CATIONIC POLYMER

(75) Inventor: Nathalie Garnier, Springfield, NJ (US)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/438,965

(22) Filed: Nov. 12, 1999

(30) Foreign Application Priority Data

Nov. 12, 1998 (FR) .............................. 98 14217

(51) Int. Cl.$^7$ ............................. C11D 1/04; C11D 3/37; C11D 9/36
(52) U.S. Cl. ....................... 510/119; 510/121; 510/122; 510/126; 510/398; 510/434; 510/466; 510/504; 510/533
(58) Field of Search ................................ 510/119, 121, 510/122, 126, 398, 434, 466, 504, 533

(56) References Cited

U.S. PATENT DOCUMENTS

| | | | |
|---|---|---|---|
| 2,261,002 A | 10/1941 | Ritter | 260/370 |
| 2,271,378 A | 1/1942 | Searle | 167/22 |
| 2,273,780 A | 2/1942 | Dittmar | 260/28 |
| 2,375,853 A | 5/1945 | Kirby | 260/583 |
| 2,388,614 A | 11/1945 | Kirby et al. | 167/22 |
| 2,454,547 A | 11/1948 | Bock | 260/567.6 |
| 2,528,378 A | 10/1950 | Mannheimer | 260/309.6 |
| 2,781,354 A | 2/1957 | Mannheimer | 260/309.6 |
| 2,961,347 A | 11/1960 | Floyd | 117/141 |
| 3,206,462 A | 9/1965 | McCarty | 260/256.4 |
| 3,227,615 A | 1/1966 | Korden | 167/87.1 |
| 3,874,870 A | 4/1975 | Green et al. | 71/67 |
| 3,929,990 A | 12/1975 | Green et al. | 424/78 |
| 3,966,904 A | 6/1976 | Green et al. | 424/78 |
| 4,001,432 A | 1/1977 | Green et al. | 424/329 |
| 4,005,193 A | 1/1977 | Green et al. | 424/168 |
| 4,025,617 A | 5/1977 | Green et al. | 424/78 |
| 4,025,627 A | 5/1977 | Green et al. | 424/248.4 |
| 4,025,653 A | 5/1977 | Green et al. | 424/325 |
| 4,026,945 A | 5/1977 | Green et al. | 267/567.6 |
| 4,027,020 A | 5/1977 | Green et al. | 424/248.56 |
| 4,693,935 A | 9/1987 | Mazurek | 428/352 |
| 4,724,851 A * | 2/1988 | Cornwall et al. | 132/7 |
| 4,728,571 A | 3/1988 | Clemens et al. | 428/352 |
| 4,972,037 A | 11/1990 | Garbe et al. | 526/245 |
| 5,034,218 A * | 7/1991 | Duvel | 424/70 |
| 5,180,584 A | 1/1993 | Sebag et al. | 424/401 |
| 5,275,755 A * | 1/1994 | Sebag et al. | 252/174.15 |
| 5,409,628 A * | 4/1995 | Heinz et al. | 252/174.17 |
| 5,439,673 A * | 8/1995 | Murray | 424/70.12 |
| 5,627,148 A | 5/1997 | Dubief et al. | 252/174.17 |
| 5,759,527 A * | 6/1998 | Patel et al. | 424/70.11 |
| 5,900,232 A | 5/1999 | Cauwet et al. | 424/70.22 |
| 5,972,356 A * | 10/1999 | Peffly et al. | 424/401 |
| 5,977,038 A * | 11/1999 | Birtwistle et al. | 510/122 |
| 5,980,877 A * | 11/1999 | Baravetto et al. | 424/70.12 |
| 6,004,545 A * | 12/1999 | Karlen et al. | 424/70.12 |
| 6,028,041 A * | 2/2000 | Decoster et al. | 510/119 |

FOREIGN PATENT DOCUMENTS

| | | |
|---|---|---|
| EP | 0 122 324 | 10/1984 |
| EP | 0 412 704 | 2/1991 |
| EP | 0 412 707 | 2/1991 |
| EP | 0 492 657 | 7/1992 |
| EP | 0 531 650 | 3/1993 |
| EP | 0 582 152 | 2/1994 |
| FR | 1 583 363 | 10/1969 |
| FR | 2 080 759 | 11/1971 |
| FR | 2 162 025 | 7/1973 |
| FR | 2 190 406 | 2/1974 |
| FR | FR 2 252 840 | 6/1975 |
| FR | 2 270 846 | 12/1975 |
| FR | 2 280 361 | 2/1976 |

(List continued on next page.)

OTHER PUBLICATIONS

Charles Todd et al., "Volatile Silicone Fluids For Cosmetic Formulations", Cosmetics and Toiletries, vol. 19, Jan. 1976, pp. 29–32.
M.R. Porter, "Handbook of Surfactants", Blackie & Son, Inc. (Glasgow and London), 1991, pp. 116–178.
English language Derwent Abstract of FR 1 583 363.
English language Derwent Abstract of FR 2 080 759.
English language Derwent Abstract of FR 2 162 025.
English language Derwent Abstract of FR 2 190 406.
English language Derwent Abstract of FR 2 252 840.
English language Derwent Abstract of FR 2 270 846.
English language Derwent Abstract of FR 2 280 361.
English language Derwent Abstract of FR 2 316 271.
English language Derwent Abstract of FR 2 320 330.
English language Derwent Abstract of FR 2 336 434.
English language Derwent Abstract of FR 2 368 508.
English language Derwent Abstract of FR 2 413 907.
English language translation of JP 04–108724.
English language translation of JP 10–203939.
English language Derwent Abstract of EP 0 531 650.

Primary Examiner—Charles Boyer
(74) Attorney, Agent, or Firm—Finnegan, Henderson Farabow, Garrett & Dunner LLP

(57) ABSTRACT

A cosmetic conditioning and detergent composition for keratinous substances, especially hair, and a process for washing the keratinous substances using the composition, wherein the composition comprises, in an aqueous medium,
(A) at least one anionic surfactant derived from a carboxylic acid, wherein the at least one anionic surfactant does not include a sulphate or sulphonate function;
(B) at least one silicone which does not include an amide function, and
(C) at least one cationic polymer which contains quaternary ammonium groups in the polymeric main chain.

29 Claims, No Drawings

FOREIGN PATENT DOCUMENTS

| | | |
|---|---|---|
| FR | 2 316 271 | 1/1977 |
| FR | 2 320 330 | 3/1977 |
| FR | 2 336 434 | 7/1977 |
| FR | 2 368 508 | 5/1978 |
| FR | 2 413 907 | 8/1979 |
| GB | 1 513 672 | 6/1978 |
| JP | 04-108724 | 4/1992 |
| JP | 10-203939 | 8/1998 |
| WO | WO 93/23009 | 11/1993 |
| WO | WO 93/23446 | 11/1993 |
| WO | WO 94/18934 | 9/1994 |
| WO | WO 94/27571 | 12/1994 |
| WO | WO 95/00578 | 1/1995 |
| WO | WO 95/03776 | 2/1995 |
| WO | 96/32919 | * 10/1996 |
| WO | WO 96/32919 | 10/1996 |
| WO | 98/19656 | * 5/1998 |
| WO | WO 98/19656 | 5/1998 |

* cited by examiner

CONDITIONING AND DETERGENT COMPOSITION COMPRISING AN ANIONIC SURFACTANT, A SILICONE, AND A CATIONIC POLYMER

The present invention relates to cosmetic conditioning and detergent compositions, and the use of such compositions, for the simultaneous care and washing of keratinous substances.

For the cleansing and/or washing of the hair and/or skin, the use of detergent compositions (shampoo or shower gel) based essentially on conventional surfactants of, in particular, anionic, nonionic and/or amphoteric type, but more particularly of anionic type, is common. These compositions are applied to wetted hair or skin and the foam generated by massaging or rubbing with the hands makes it possible, after rinsing with water, to remove the various types of dirt initially present on the hair or skin.

These base compositions can have good washing power, but their attendant intrinsic cosmetic properties, however, are fairly weak. The relatively aggressive nature of cleansing treatments using those conventional surfactants may, in the long term, result in more or less marked damage to the keratinous substances. The damage is associated, in particular, with the gradual removal of the lipids or proteins present in or on the surface of these substances.

In order to improve the cosmetic properties of the above detergent compositions, and more particularly those detergent compositions which are required to be applied to sensitized hair (i.e. hair which is damaged or embrittled under the chemical effect, in particular, of atmospheric agents and/or hair treatments, such as permanent-waving, dyeing or bleaching), it is now customary to introduce into these compositions additional cosmetic agents, known as conditioners, which are intended primarily to repair or limit the harmful or undesirable effects brought about by the various treatments or attacks to which the hair fibers are more or less repeatedly subjected. These conditioners may of course also improve the cosmetic comportment of natural hair.

Conditioners most commonly used in shampoos are cationic polymers, silicones and/or silicone derivatives that impart to the washed, dry, or wetted hair, increased ease in disentangling, softness, and smoothing relative to corresponding cleansing compositions without these conditioners.

Despite the progress recently achieved in the field of shampoos based on cationic polymers, in particular the cationic derivatives of cellulose or of guar gum and of silicone, these conditioners do not provide complete satisfaction, so that a need still exists for products exhibiting better performance levels in terms of one or more of the abovementioned cosmetic properties.

According to British patent application GB-A-1513672, strongly cationic polymers can be used in compositions for the washing or care of hair in order to facilitate disentangling of the hair and to impart softness and manageability to it. The use of these cationic polymers for that purpose, however, presents a variety of disadvantages. These polymers undergo significant deposition in the course of repeated use because of their strong affinity for the hair, leading to undesirable effects such as an unpleasant feel, a tautening of the hair, and an inter-fiber adhesion which affects styling. These disadvantages are more marked in the case of fine hair, which lacks shape retention, vitality and body.

An object of the present invention is to overcome the abovementioned disadvantages by providing conditioning and detergent compositions which have sufficient foaming properties and exhibit good conditioning properties, for example disentangling, softness and sheen properties, without conferring greasiness, heaviness or an unpleasant feel.

Following much research carried out into this matter, the inventor has now discovered, entirely unexpectedly and surprisingly, that by combining a non-amido functional silicone and a specific cationic polymer with an anionic surfactant of carboxylic type it is possible to obtain detergent compositions that can have excellent cosmetic properties, for example disentangling, softness, sheen and volume properties for the keratinous substances treated, while retaining the good intrinsic washing power and foaming power of the compositions.

These new compositions make it possible to deposit a large quantity of silicone on the keratinous substances (e.g., hair) without a greasy feel or appearance.

The compositions in accordance with the invention can impart to keratinous substances, especially hair, a notable treatment effect which is manifested, for example, in ease of disentangling as well as providing body, lightness, smoothing, softness and manageability without any heaviness.

These effects-are entirely unexpected. The inventor has in fact found that the addition of the cationic polymers described below to shampoo compositions based on sulphate surfactant and silicone did not improve the cosmetic properties of the composition and that, on the contrary, load effects appeared.

The present invention relates to new cosmetic conditioning and detergent compositions comprising, in an aqueous medium, (A) at least one anionic surfactant of carboxylic type which does not include a sulphate or sulphonate function, (B) at least one silicone which does not include an amide function, and (C) at least one cationic polymer which contains quaternary ammonium groups in the main chain.

The present invention additionally relates to the use of the composition according to the invention for the simultaneous care and washing of keratinous substances such as the hair and skin.

The present invention will now be described in detail.

Examples of the anionic surfactants of carboxylic type, i.e., anionic surfactants derived from a carboxylic acid and which do not include a sulphate or sulphonate function, that can be used in compositions according to this invention include: alkyl-D-galactoside-uronic acids and their salts; polyalkoxylated $C_6$–$C_{24}$-alkyl ether carboxylic acids; polyalkoxylated ($C_6$–$C_{24}$-alkyl)aryl ether carboxylic acids; polyalkoxylated $C_6$–$C_{24}$-alkylamido ether carboxylic acids and their salts; including those containing from 2 to 50 alkylene oxide groups such as ethylene oxide groups; ($C_6$–$C_{24}$-acyl) sarcosinates; ($C_6$–$C_{24}$-acyl)- glutamates; and the esters of carboxylic ($C_6$–$C_{24}$-alkyl)polyglycosides, such as alkylglucoside citrates and alkylpolyglycoside tartrates. The esters of carboxylic polyglycosides are sold, for example, under the names EUCAROL APG/EC and EUCAROL APG/ET by the LAMBERTI company.

It is also possible to use mixtures of these surfactants. Accordingly, the term "chosen from" as it is used hereinafter implies that mixtures of the listed elements may be chosen, in addition to the individual elements.

In one embodiment of the invention, the anionic surfactants of carboxylic type are chosen from polyalkoxylated $C_6$–$C_{24}$-alkyl ether carboxylic acids; polyalkoxylated $C_6$–$C_{24}$-alkylamido ether carboxylic acids, for example, those containing from 2 to 15 alkylene oxide groups; and ($C_6$–$C_{24}$-alkyl)polyglycoside-carboxylic esters.

Silicones that can be used in accordance with the invention may be soluble or insoluble in water or in the final composition. They may be volatile or nonvolatile.

Examples of silicones that can be used in accordance with the invention include organopolysiloxanes which are insoluble in the composition and which may be in the form of oils, waxes, resins or gums.

Organopolysiloxanes are defined in greater detail in the work by Walter NOLL entitled "Chemistry and Technology of Silicones" (1968, Academic Press), the disclosure of which is hereby incorporated by reference. They may be volatile or nonvolatile.

When volatile, the silicones can be chosen from silicones having a boiling point ranging from 60° C. to 260° C., including, but not limited to the cyclic and linear volatile silicones listed below at (i) and (ii), respectively:

(I) Cyclic silicones containing 3 to 7 silicon atoms. In one embodiment of the invention, the cyclic silicones contain from 4 to 5 silicon atoms. Such a silicone is, for example, the octamethylcyclotetrasiloxane sold under the name "VOLATILE SILICONE 7207" by UNION CARBIDE or "SILBIONE® 70045 V 2" by RHONE POULENC; the decamethylcyclopentasiloxane sold under the name "VOLATILE SILICONE 7158" by UNION CARBIDE or "SILBIONE® 70045 V 5" by RHONE POULENC; and mixtures thereof.

Other examples of such cyclic silicones include the cyclic copolymers of the dimethylsiloxane/methylalkylsiloxane type, such as "SILICONE VOLATILE FZ 3109" sold by UNION CARBIDE, of chemical structure:

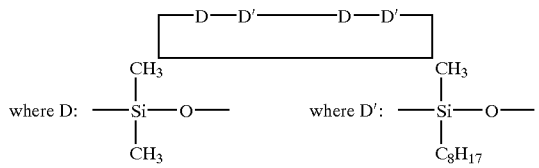

Mixtures of cyclic silicones with organosilicon compounds, such as the mixture of octamethylcyclotetrasiloxane and tetratrimethylsilylpentaerythritol (50/50) and the mixture of octamethylcyclotetrasiloxane and 1,1'-oxybis{(2, 2,2', 2', 3,3'-hexa(trimethylsilyloxy))-neopentane}, can also be used in accordance with the invention;

(ii) Linear volatile silicones having 2 to 9 silicon atoms and a viscosity of less than or equal to $5 \times 10^{-6}$ m$^2$/s at 25° C. Such a compound is, for example, the decamethyltetrasiloxane sold under the name "SH 200" by TORAY SILICONE. Silicones from this class are also described in the article published in Cosmetics and Toiletries, Vol. 91, January 76, pp. 27–32—TODD & BYERS "Volatile Silicone Fluids for Cosmetics", the disclosure of which is hereby incorporated by reference.

The nonvolatile silicones which can be used in accordance with the present invention include:

(i) polyalkylsiloxanes;
(ii) polyarylsiloxanes;
(iii) polyalkylarylsiloxanes;
(iv) silicone gums;
(v) silicone resins;
(vi) polyorganosiloxanes comprising in their structure at least one organic functional group attached directly to the siloxane chain or attached via a hydrocarbon radical;

(vii) block copolymers comprising a linear polysiloxane-polyoxyalkylene block as repeating units;

(viii) graft silicone polymers comprising a non-silicone organic framework; and an organic main chain formed from non-silicone organic monomers and onto which there is grafted, within the chain and optionally at least one of its ends, at least one polysiloxane macromonomer;

(ix) graft silicone polymers comprising a polysiloxane framework grafted with non-silicone organic monomers, which comprise a polysiloxane main chain to which there is grafted, within the chain and optionally at least one of its ends, at least one non-silicone organic macromonomer; and (x) mixtures thereof.

Representative examples of useful polyalkylsiloxanes include:

linear polydimethylsiloxanes having terminal trimethylsilyl groups, such as, for example, and without limitation, the SILBIONE® oils of the 70047 series which are sold by RHONE POULENC, the oil SILBIONE® 47 V 500 000 from RHONE POULENC, or certain VISCASILs from GENERAL ELECTRIC (Viscosil 60.000), the DC 200 FLUIDs from DOW CORNING, or the silicone oil AK 300.000 from WACKER;

linear polydimethylsiloxanes having terminal hydroxydimethylsilyl groups, such as the oils from the 48 V series from RHONE POULENC.

Included in this class of polyalkylsiloxanes are poly $C_1$–$C_{20}$-alkyl siloxanes sold by GOLDSCHMIDT under the trade names ABILWAX® 9800 and ABILWAX® 9801.

Examples of polyalkylarylsiloxanes useful in compositions in accordance with the present invention include linear or branched polydimethylmethylphenylsiloxanes or polydimethyldiphenylsiloxanes, such as DC 556 COSMETIC GRADE FLUID from DOW CORNING.

Silicone gums in accordance with the invention are polyorganosiloxanes having a number-average molecular mass ranging from 200,000 to 1,000,000. The silicone gums can be used alone or in a mixture in a solvent. The solvent can be chosen from volatile silicones, polydimethylsiloxane (PDMS) oils, polyphenylmethylsiloxane (PPMS) oils, isoparaffins, polyisobutylenes, methylene chloride, pentane, dodecane, and tridecanes.

Examples of silicone gums include:
polydimethylsiloxane
poly((dimethylsiloxane)/(methylvinylsiloxane)),
poly((dimethylsiloxane)/(diphenylsiloxane)),
poly((dimethylsiloxane)/(phenylmethylsiloxane)), and
poly((dimethylsiloxane)/(diphenylsiloxane)/(methylvinylsiloxane)).

Examples of mixtures of silicone gums include:

1) mixtures formed from a polydimethylsiloxane hydroxylated at the chain end (DIMETHICONOL in accordance with the CTFA nomenclature) and a cyclic polydimethylsiloxane (CYCLOMETHICONE in accordance with the CTFA nomenclature) such as Q2 1401 sold by DOW CORNING;

2) mixtures formed from a polydimethylsiloxane gum with a cyclic silicone, such as SF 1214 SILICONE FLUID from GENERAL ELECTRIC, which is an SE 30 gum of molecular weight 500,000 dissolved in SF 1202 SILICONE FLUID (decamethylcyclopentasiloxane);

3) mixtures of two polydimethylsiloxanes (PDMS) differing in viscosity, for example, mixtures of a PDMS gum and a PDMS oil, such as SF 1236 and CF 1241 from GENERAL ELECTRIC. The product SF 1236 is a mixture of an SE 30 gum defined above, of viscosity 20 m²/s, and an SF 96 oil of viscosity 5×10⁻⁵ m²/s (15% of gum SE 30 and 85% of oil SF 96). The product CF 1241 is the mixture of an SE 30 gum (33%) and a PDMS (67%) of viscosity 10⁻³ m²/s.

In one embodiment of the invention, the silicone resins in accordance with the invention are crosslinked siloxane systems comprising at least one unit chosen from $(R)_2SiO_{2/2}$, $RSiO_{3/2}$, and $SiO_{4/2}$, in which R is chosen from hydrocarbon groups having 1 to 6 carbon atoms and phenyl groups. In another embodiment of the invention, the silicone resins are chosen from those in which R is chosen from lower alkyl radicals and phenyl radicals.

Examples of these silicone resins include the product sold under the name DOW CORNING 593 by DOW CORNING or those sold under the name SILICONE FLUID SS 4267 by GENERAL ELECTRIC, which are dimethyl/trimethylpolysiloxanes.

The organomodified polyorganosiloxanes of the invention are polysiloxanes as defined above which include in their structure at least one organofunctional groups attached directly to the siloxane chain or attached via a hydrocarbon radical.

Examples of these organomodified polysiloxanes include polysiloxanes comprising:

a) polyethyleneoxy and/or polypropyleneoxy groups, optionally including alkyl groups, such as the product called lauryl methicone copolyol sold under the name Q2 5200 by DOW CORNING;

b) (per)fluorinated groups, such as trifluoroalkyl groups, as sold, for example, by SHIN ETSU under the name FL 100;

c) thiol groups;

d) carboxylate groups, such as the products described in European Patent EP 185 507 to CHISSO CORPORATION;

e) hydroxyl groups, such as the hydroxyalkyl-functional polyorganopolysiloxanes described in French Patent Application FR 85-16334 and in particular the y-hydroxypropyl-functional polyorganopolysiloxanes;

f) alkoxy groups containing at least 12 carbon atoms, such as the product SILICONE COPOLYMER F755 from SWS SILICONES and the products ABILWAX® 2428, ABILWAX® 2434, ABILWAX® 2440 from GOLDSCHMIDT;

g) acyloxyalkyl groups containing at least 12 carbon atoms, such as the polyorganosiloxanes described in French Patent Application FR 88-17433, and in particular the stearoyloxypropyl-functional polyorganosiloxanes;

h) amphoteric groups;

i) bisulphite groups;

j) substituted or unsubstituted amino groups, such as the products sold under the name GP 4 Silicone Fluid and GP 7100 by GENESEE or the products sold under the names Q2 8220 and DOW CORNING 929 or 939 by DOW CORNING. The substituted amino groups can be, for example, $C_1$–$C_4$ alkylamino groups. In one embodiment of the invention, the silicones are chosen from the compounds called amodimethicone and trimethylsilylamodimethicone in accordance with the CTFA naming ($7^{th\ Ed.}$ 1997).

In one embodiment of the invention, the block copolymers having a linear polysiloxane-polyoxyalkylene block as repeating units have the following formula:

$$((Y(R_2SiO)_aR'_2SiYO)((Cn\ H_{2n}O)_b))_c \qquad (V)$$

in which:

R and R', which are identical or different, are chosen from monovalent hydrocarbon radicals which do not contain aliphatic unsaturation, n is an integer from 2 to 4, a is an integer greater than or equal to 5; in one embodiment of the invention, a ranges from 5 to 200 and in another embodiment of the invention, a ranges from 5 to 100, b is an integer greater than or equal to 4; in one embodiment of the invention, b ranges from 4 to 200 and in another embodiment, b ranges from 5 to 100, c is an integer greater than or equal to 4; in one embodiment of the invention, c ranges from 4 and 1000 and in another embodiment c ranges from 5 to 300, Y is chosen from divalent organic groups and is connected to the adjacent silicon atom via a carbon-silicon bond and to the polyoxyalkylene block via an oxygen atom, the average molecular weight of each siloxane block ranges from approximately 400 to approximately 10,000, the weight of each polyoxyalkylene block ranging from approximately 300 to approximately 10,000, the siloxane blocks are present in the block copolymer in an amount ranging from approximately 10% to approximately 95% by weight of the block copolymer, the weight-average molecular weight of the block copolymer is at least 3000; in one embodiment of the invention, the weight-average molecular weight of the block copolymer ranges from 5000 to 1,000,000 and in another embodiment of the invention the weight-average molecular weight of the block copolymer ranges from 10,000 to 200,000.

In one embodiment of the invention, R and R' are chosen from: alkyl radicals such as, for example, the methyl, ethyl, propyl, butyl, pentyl, hexyl, octyl, decyl, and dodecyl radicals; aryl radicals such as, for example, phenyl and naphthyl; aralkyl radicals such as, for example, benzyl and phenylethyl; and the tolyl, xylyl, and cyclohexyl radicals.

In one embodiment of the invention, Y is chosen from —R"—, —R"—CO—, in which R" is chosen from: divalent alkylene groups such as, for example, ethylene, propylene and butylene; and divalent arylene groups such as —$C_6H_4$—, —$C_6H_4$—$C_6H_4$—, —$C_6H_4$—$CH_2$—$C_6H_4$—, —$C_6H_4$—$C(CH_3)_2$—$C_6H_4$. In another embodiment of the invention, Y is chosen from the divalent alkylene radicals —$CH_2$—$CH_2$—$CH_2$— and $C_4H_8$.

The preparation of the block copolymers used in accordance with the present invention is described in the European Application EP 0 492 657 A1, the disclosure of which is herein incorporated by reference.

The polymers having a non-silicone organic framework which is grafted with monomers containing a polysiloxane, in accordance with the invention, can be selected from those described in U.S. Pat. Nos. 4,693,935, 4,728,571, and 4,972,037, European patent applications EP-A-0 412 704, EP-A-0 412 707, EP-A-0 640 105 and international application WO 95/00578. The disclosures of each of the above-listed documents are hereby incorporated by reference. The described polymers are copolymers obtained by free-radical polymerization from ethylenically unsaturated monomers and silicone macromers having a terminal vinyl group, or copolymers obtained by reaction of a polyolefin containing functionalized groups and of a polysiloxane macromer having a terminal function which is reactive with the said functionalized groups.

Examples of polymers having a polysiloxane framework grafted with non-silicone organic monomers that are suitable for use in the present invention, and the particular way in which they are prepared, are described in European patent application EP-A-0 582 152, and international patent applications WO 93/23009 and WO 95/03776, the disclosures of which are hereby incorporated by reference.

According to the invention, all of the silicones can also be used in the form of emulsions or microemulsions.

In one embodiment of the invention, the silicones in accordance with the invention are chosen from:

nonvolatile silicones selected from the class of polyalkylsiloxanes having terminal trimethylsilyl groups, such as: oils having a viscosity of between 0.2 and 2.5 m$^2$/s at 25° C., oils from the series DC200 from DOW CORNING, oils from the series SILBIONE® 70047 and 47, such as oils in this series having a viscosity of 60,000 cSt and the oil 70 047 V 500 000 sold by RHONE POULENC; polyalkylsiloxanes having terminal dimethylsilanol groups, for example the dimethiconols or polyalkylarylsiloxanes such as the oil SILBIONE® 70641 V 200 sold by RHONE POULENC;

mixtures of organopolysiloxanes and cyclic silicones, such as the product Q2 1401 sold by DOW CORNING and the product SF 1214 sold by GENERAL ELECTRIC;

mixtures of two PDMS having different viscosities, in particular a gum and an oil, such as the product SF 1236 sold by GENERAL ELECTRIC;

the organopolysiloxane resin sold under the name DOW CORNING 593; and polysiloxanes containing amino groups, such as amodimethicones and trimethylsilylamodimethicones.

According to the invention, the silicone or silicones are present in the composition in an amount ranging from 0.05% to 10% by weight, relative to the total weight of the composition. In one embodiment of the invention, the amount ranges from 0.1% to 5% by weight, relative to the total weight of the composition. In another embodiment of the invention, the amount ranges from 0.5% to 3% by weight, relative to the total weight of the composition.

The cationic polymers which contain quaternary ammonium groups in the polymeric main chain can be chosen from those described in (1)–(8) below (1) Quaternary diammonium polymers containing repeating units of the formula:

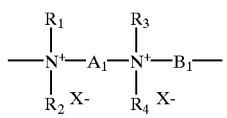

(I)

in which:

R$_1$, R$_2$, R$_3$ and R$_4$, which are identical or different, are chosen from aliphatic, alicyclic, and arylaliphatic radicals containing 1 to 20 carbon atoms or lower hydroxyalkyl aliphatic radicals; or else R$_1$, R$_2$, R$_3$ and R$_4$, together or separately, together with the nitrogen atoms to which they are attached, form heterocycles optionally containing a second heteroatom other than nitrogen; or else R$_1$, R$_2$, R$_3$ and R$_4$ are chosen from linear and branched C$_1$-C, alkyl radicals substituted by a group chosen from nitrile, ester, acyl, amide, —CO—O—R$_5$—D, and —CO—NH—R$_5$—D groups, wherein R$_5$ is an alkylene and D is a quaternary ammonium group;

A$_1$ and B$_1$ are chosen from linear and branched, saturated and unsaturated, polymethylene groups which contain 2 to 20 carbon atoms, and can contain, bonded to or intercalated in the main chain, at least one aromatic rings, or at least one of an oxygen atom, a sulphur atom, and sulphoxide, sulphone, disulphide, amino, alkylamino, hydroxyl, quaternary ammonium, ureido, amide, and ester groups, and X$^-$ is chosen from anions derived from a mineral or organic acid;

A$_1$, R$_1$ and R$_3$ can, together with the two nitrogen atoms to which they are attached, form a piperazine ring; and, if A$_1$ is a linear or branched, saturated or unsaturated alkylene or hydroxyalkylene radicals, B$_1$ may also be a group (CH$_2$)$_n$—CO—D—OC—(CH$_2$)$_n$—in which D is chosen from:

a) a glycol residue of formula —O—Z—O—, in which Z is chosen from linear and branched hydrocarbon radicals and a group corresponding to one of the following formulae:

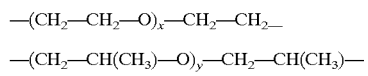

in which x and y are integers from 1 to 4, representing a defined and single degree of polymerization, or any number from 1 to 4, representing an average degree of polymerization;

b) a bis-secondary diamine residue, such as a piperazine derivative;

c) a bis-primary diamine residue of formula —NH—Y—NH—, in which Y is chosen from linear and branched hydrocarbon radicals and the divalent radical —CH$_2$—CH$_2$—S—S—CH$_2$—CH$_2$—; and d) a ureylene group of formula —NH—CO—NH—.

In one embodiment of the invention, X$^-$ is an anion such as chloride or bromide.

These polymers have a number-average molecular mass which is generally between 1000 and 1,000,000.

Polymers of this type are described in French Patents 2,320,330, 2,270,846, 2,316,271, 2,336,434 and 2,413,907 and in U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020. The disclosures of each of these French and United States patents are hereby incorporated by reference.

For example, it is possible to use polymers which comprise repeating units corresponding to the formula:

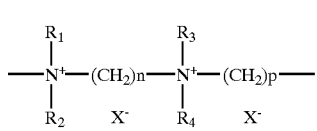

(a)

in which R$_1$, R$_2$, R$_3$ and R$_4$, which are identical or different, are chosen from alkyl and hydroxyalkyl radicals having approximately 1 to 4 carbon atoms, n and p are integers ranging from approximately 2 to 20, and X⁻ is an anion derived from a mineral or organic acid.

In one embodiment of the invention, the composition of formula (a) is that for which $R_1$, $R_2$, $R_3$ and $R_4$ are each a methyl radical, n is 3, p is 6, and X is Cl, which is known as hexadimethrine chloride in accordance with the INCI (CTFA) nomenclature.

(2) Quaternary polyammonium polymers comprising units of formula (II):

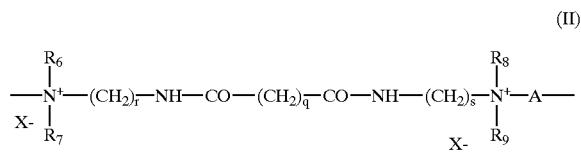

(II)

in which:

$R_6$, $R_7$, $R_8$ and $R_9$, which are identical or different, are chosen from a hydrogen atom, methyl, ethyl, propyl, β-hydroxyethyl, β-hydroxypropyl, and —CH$_2$CH$_2$(OCH$_2$CH$_2$)$_p$OH radicals, in which p is an integer ranging from 0 to 6, with the proviso that $R_6$, $R_7$, $R_8$ and $R_9$ are not simultaneously a hydrogen atom, r and s, which are identical or different, are integers ranging from 1 to 6, q is an integer ranging from 0 to 34, X is chosen from halogen atoms, A is a radical of a dihalide or, preferably, —CH$_2$—CH$_2$—O—CH$_2$—CH$_2$—.

Such compounds are described in the European patent application EP-A-122 324, the disclosure of which is hereby incorporated by reference.

Examples of these compounds include the products "MIRAPOL A 15", "MIRAPOL AD1", "MIRAPOL AZ1" and "MIRAPOL 175" sold by MIRANOL.

(3) Polymers comprising piperazinyl units and radicals, and the oxidation and/or quaternization products of these polymers, wherein the radicals are chosen from divalent straight-chain and branched hydroxyalkylene and alkylene radicals, optionally interrupted by oxygen, sulphur or nitrogen atoms or by aromatic or heterocyclic rings. Such polymers are described in French patents 2,162,025 and 2,280,361, the disclosures of which are hereby incorporated by reference.

(4) Water-soluble polyaminoamides prepared, for example, by polycondensation of an acid compound with a polyamine. These polyaminoamides can be crosslinked by an epihalohydrin, a diepoxide, a dianhydride, an unsaturated anhydride, a diunsaturated derivative, a bishalohydrin, a bisazetidinium, a bishaloacyldiamine, a bisalkyl halide or else by an oligomer resulting from the reaction of a bifunctional compound which is reactive with respect to a bishalohydrin, a bisazetidinium, a bishaloacyidiamine, a bisalkyl halide, an epihalohydrin, a diepoxide or a diunsaturated derivative; the crosslinking agent is used in proportions ranging from 0.025 to 0.35 mol per amine group of the polyaminoamide. These polyamino-polyamides can be alkylated or, if they include at least one tertiary amine function, can be quaternized. Such polymers are described in French patents 2,252,840 and 2,368,508, the disclosures of which are hereby incorporated by reference.

(5) Polyaminoamide derivatives resulting from the condensation of polyalkylene polyamines with polycarboxylic acids followed by alkylation with bifunctional agents. Examples include, but are not limited to, adipic acid-dialkylaminohydroxyalkyldialkylenetriamine polymers in which the alkyl radical contains 1 to 4 carbon atoms such as methyl, ethyl, and propyl. Such polymers are described in French patent 1,583,363, the disclosure of which is hereby incorporated by reference.

In one embodiment of the invention, the derivative used is an adipic acid/dimethylaminohydroxypropyl/diethylenetriamine polymer sold under the name CARTARETINE F, F4 or F8 by SANDOZ.

(6) Polymers obtained by reacting a polyalkylene-polyamine containing two primary amine groups and at least one secondary amine group with a dicarboxylic acid chosen from diglycolic acid and saturated aliphatic dicarboxylic acids having 3 to 8 carbon atoms, the molar ratio of the polyalkylene-polyamine to the dicarboxylic acid ranging from 0.8:1 to 1.4:1; the resulting polyaminoamide being reacted with epichlorohydrin in a molar ratio ranging from 0.5:1 and 1.8:1 of epichlorohydrin relative to the secondary amine group of the polyaminoamide. Such polymers are described in U.S. Pat. Nos. 3,227,615 and 2,961,347, the disclosures of which are hereby incorporated by reference. Polymers of this type are sold, for example, under the name "HERCOSETT 57" by HERCULES Inc. and under the name "PD 170" or "DELSETTE 101" by HERCULES Inc. in the case of the adipic acid/epoxypropyl/diethylene-triamine copolymer.

(7) Alkyldiallylamine and dialkyldiallylammonium cyclic polymers, such as the homopolymers and copolymers containing, as principal constituent of the chain, units corresponding to the formulae (VI) or (VI').

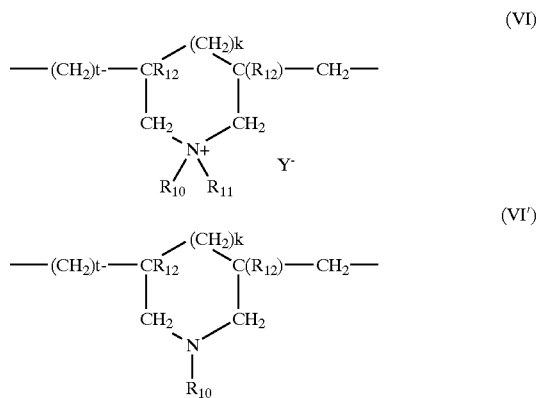

in which, for both (VI) and (VI'), k and t are 0 or 1, the sum k+t being equal to 1; $R_{12}$ is chosen from a hydrogen atom and a methyl radical; $R_{10}$ and $R_{11}$, which can be identical or different, are chosen from alkyl groups having 1 to 22 carbon atoms; hydroxyalkyl groups, wherein in one embodiment of the invention the alkyl groups have 1 to 5 carbon atoms; lower (C$_1$–C$_4$) amidoalkyl groups; or, in formula (VI), $R_{10}$ and $R_{11}$, in conjunction with the nitrogen atom to which they are attached, form a heterocyclic group, and, in formula (VI'), $R_{10}$, in conjunction with the nitrogen atom to which it is attached, forms a heterocyclic group, such as piperidinyl and morpholinyl; Y⁻is chosen from anions such as bromide, chloride, acetate, borate, citrate, tartrate, bisulphate, bisulphite, sulphate, and phosphate. These polymers are described in French Patent 2,080,759 and in its certification of addition 2,190,406, the disclosures of which are herein incorporated by reference.

In one embodiment of the invention $R_{10}$ and $R_{11}$, which can be identical or different, are chosen from alkyl groups having 1 to 4 carbon atoms.

In one embodiment of the invention, the polymers defined above are chosen from dimethyidiallylammonium chloride homopolymer sold under the name "MERQUAT 100" by CALGON (and its homologues of low weight-average molecular masses) and the diallyldimethylammonium chloride-acrylamide copolymers sold under the name "MERQUAT 550".

(8) Quaternary polymers of vinylpyrrolidone and vinylimidazolium such as, for example, the products sold under the names Luviquat® FC 905, FC 550 and FC 370 by BASF.

According to the invention, the cationic polymer or polymers are present in the composition in an amount ranging from 0.005% to 10% by weight, relative to the total weight of the composition. In one embodiment of the invention, the amount of cationic polymer or polymers ranges from from 0.01% to 5% by weight, relative to the total weight of the composition. In another embodiment of the invention, the amount of cationic polymer or polymers ranges from 0.1% to 3% by weight, relative to the total weight of the composition.

The compositions of the invention may additionally and advantageously contain at least one other surfactant, selected from anionic surfactants of phosphate, sulphonate and/or sulphate type, amphoteric surfactants, nonionic surfactants, cationic surfactants or mixtures thereof.

The additional surfactants suitable for implementation of the present invention are, in particular, the following:

(i) Anionic surfactant(s)

Examples include the following compounds: alkyl sulphates, alkyl ether sulphates, alkylamido ether sulphates, alkylaryl polyether sulphates, monoglyceride sulphates, $C_6$–$C_{24}$-alkyl sulphosuccinates, $C_6$–$C_{24}$-alkyl ether sulphosuccinates, $C_6$–$C_{24}$-alkylamide sulphosuccinates; $C_6$–$C_{24}$-alkyl sulphoacetates; alkylsulphonates, alkyl phosphates, alkylamidesulphonates, alkylarylsulphonates, α-olefin- sulphonates, paraffinsulphonates; alkyl ether phosphates; alkyl sulphosuccinamates, acyl isethionates, and acyl taurates. In one embodiment of the invention, the various alkyl radicals are chosen from those containing 8 to 24 carbon atoms and the aryl radicals are chosen from phenyl and benzyl groups. The salts can be chosen, for example, from alkali metal salts, such as sodium salts, ammonium salts, amine salts, salts of amino alcohols, and magnesium salts.

(ii) Nonionic surfactant(s)

Nonionic surfactants themselves are also compounds which are well known per se (in this respect see, in particular, "Handbook of Surfactants" by M. R. PORTER, published by Blackie & Son (Glasgow and London), 1991, pp. 116–178, the disclosure of which is hereby incorporated by reference). Non-limiting examples of nonionic surfactants include alcohols, alpha-diols, alkylphenols, and polyethoxylated, polypropoxylated, and polyglycerolated fatty acids which have a fatty chain containing, for example, 8 to 18 carbon atoms, wherein the number of ethylene oxide and propylene oxide groups ranges, in one embodiment, from 2 to 50 and wherein the number of glycerol groups ranges, in one embodiment, from 2 to 30. Other non-limiting examples include copolymers of propylene and ethylene oxide, the condensates of propylene and ethylene oxide with fatty alcohols; polyethoxylated fatty amides having, in one embodiment of the invention, 2 to 30 mol of ethylene oxide, polyglycerolated fatty amides containing on average from 1 to 5 glycerol groups and, in one embodiment of the invention, from 1.5 to 4; polyethoxylated fatty amines having, in one embodiment of the invention, 2 to 30 mol of ethylene oxide; ethoxylated fatty acid esters of sorbitan having from 2 to 30 mol of ethylene oxide; sucrose fatty acid esters, polyethylene glycol fatty acid esters, alkyl polyglycosides, and N-alkyl glucamine derivatives, amine oxides such as $C_{10}$–$C_{14}$-alkylamine oxides and N-acylaminopropylmorpholine oxides. In one embodiment of the invention the nonionic surfactants in accordance with the invention are chosen from alkyl polyglycosides.

(iii) Amphoteric surfactant(s)

Examples of the additional amphoteric surfactants include derivatives of secondary and tertiary aliphatic amines in which the aliphatic radical is chosen from linear and branched chains containing 8 to 22 carbon atoms and containing at least one water-solubilizing anionic group (for example carboxylate, sulphonate, sulphate, phosphate, and phosphonate group); other amphoteric surfactants useful in the present invention include $C_8$–$C_{20}$-alkyl betaines, sulphobetaines, $C_8$–$C_{20}$-alkylamido-$C_1$–$C_6$-alkyl betaines, and $C_8$–$C_{20}$alkylamido-$C_1$–$C_6$-alkyl sulphobetaines.

Among the amine derivatives, non-limiting examples include the products sold under the name MIRANOL, such as are described in U.S. Pat. Nos. 2,528,378 and 2,781,354, the disclosures of which are hereby incorporated by reference. The structures of these particular amine correspond to:

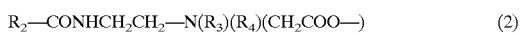

$$R_2\text{---CONHCH}_2\text{CH}_2\text{---N}(R_3)(R_4)(CH_2COO\text{---}) \qquad (2)$$

in which: $R_2$ is chosen from: alkyl radicals derived from an acid, $R_2$—COOH, present in hydrolysed copra oil; and a heptyl, nonyl, or undecyl radical, $R_3$ is a beta-hydroxyethyl group, and $R_4$ is a carboxymethyl group; and

$$R_5\text{---CONHCH}_2\text{CH}_2\text{---N(B)(C)} \qquad (3)$$

in which:

B is —$CH_2CH_2OX'$, wherein C is —$(CH_2)_z$—Y', wherein z is 1 or 2,

X' is chosen from the group —$CH_2CH_2$–COOH and a hydrogen atom,

Y' is chosen from —COOH and the radical —$CH_2$—CHOH—$SO_3$H, $R_5$ is chosen from alkyl radicals of an acid, $R_9$—COOH, which is present in copra oil and in hydrolysed linseed oil; alkyl radicals which, in one embodiment of the invention are chosen from $C_7$, $C_9$, $C_{11}$, and $C_{13}$ alkyl, and $C_{17}$ alkyl radical and its isoform, and an unsaturated $C_{17}$ radical.

These compounds are classified in the CTFA dictionary, $5^{th}$ Edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, cocoamphodipropionic acid.

An example of these compounds is the cocoamphodiacetate sold under the trade name MIRANOL® C2M in concentrated form by RHONE POULENC.

In one embodiment of the invention, anionic salts are chosen from salts of $C_8$–$C_{14}$-alkyl and ether sulphates. In another emodiment of the invention, anionic salts are chosen from $C_{12}$–$C_{14}$-alkyl and ether sulphates. These salts can comprise from 2 to 5 ethylene oxide groups and in one embodiment of the invention, the anionic surfactant is chosen from sodium, triethanolamine, and ammonium $C_{12}$–$C_{14}$-alkyl ether sulphates which are ethoxylated with approximately 2.2 mol of ethylene oxide.

In an embodiment of the present invention, the amphoteric surfactants are chosen from those belonging to the group of the betaines, for example alkyl betaines such as the cocoyl betaine sold under the name "DEHYTON AB 30" as an aqueous solution containing 30% of a.s. by HENKEL and the alkylamido betaines such as TEGOBETAINE® F50 sold by GOLDSCHMIDT.

The anionic surfactant(s) of carboxylate type are generally present in a proportion of from 3 to 50% by weight, preferably from 3 to 20% by in anweight, relative to the total weight of the composition.

When additional anionic surfactant(s), i.e., not derived from a carboxylic acid, are included in the inventive composition, they are present in the composition in an amount ranging from 1 to 30% by weight, relative to the total weight of the composition. In one embodiment of the invention, the amount of the at least one additional anionic surfactant ranges from 3 to 15% by weight, relative to the total weight of the composition.

When amphoteric and/or nonionic surfactant(s) are included in the inventive composition, such surfactants are present in the composition in an amount ranging from 0.5 to approximately 15% by weight, relative to the total weight of the composition. In one embodiment of the invention the amount ranges from 1 to 5% by weight, relative to the total weight of the composition.

The ratio by weight of the anionic surfactant(s) of carboxylate type to the entirety of the surfactants can vary from 0.1:1 to 1:1 and, in one embodiment, from 0.2:1 to 1:1.

In the composition according to the present invention, the entirety of the surfactants is present in the composition in an amount ranging from 3 to 50% by weight and, in another embodiment, from 5 to 30% by weight relative to the total weight of the composition.

The cosmetically acceptable aqueous medium can be water alone or in a mixture of water and a cosmetically acceptable solvent such as a $C_1$–$C_4$ lower alcohols, and alkylene glycols. The lower alcohols can be, for example, ethanol, isopropanol, tert-butanol, and n-butanol. The alkylene glycols can be, for example, propylene glycol and glycol ethers.

The detergent compositions according to the invention have a final pH ranging from 3 to 10. In one embodiment of the invention the final pH ranges from 5 to 8. The pH can be adjusted to the desired value conventionally by adding a base (organic or inorganic) to the composition, for example sodium hydroxide, aqueous ammonia or a primary, secondary or tertiary (poly)amine such as monoethanolamine, diethanolamine, triethanolamine, isopropanolamine or 1,3-propanediamine, or else by adding an acid, preferably a carboxylic acid such as, for example, citric acid.

The compositions in accordance with the invention may in addition to the combination defined above comprise viscosity regulators such as electrolytes, or thickeners. These viscosity regulators can be, for example, sodium chloride, sodium xylene sulphonate, scleroglucanes, xanthan gums, fatty acid alkanolamides, alkyl ether carboxylic acid alkanolamides optionally ethoxylated with up to 5 mol of ethylene oxide, such as the product sold under the name "AMINOL A15" by the company CHEM Y, crosslinked polyacrylic acids and crosslinked acrylic acid/$C_{10}$—$C_{30}$ alkyl acrylate copolymers. These viscosity regulators are used in the compositions according to the invention in in amounts which can range up to 10% by weight relative to the total weight of the composition.

The compositions in accordance with the invention may also contain up to 5% of pearlizing or opacifying agents which are well known in the state of the art, such as, for example, sodium or magnesium palmitates, sodium or magnesium stearates and hydroxystearates, fatty-chain acyl derivatives such as ethylene glycol, and polyethylene glycol monostearates and distearates, I? fatty alcohols, fatty-chain ethers such as, for example, distearyl ether or 1-(hexadecyloxy)-2-octadecanol.

The compositions in accordance with the invention may optionally further comprise other agents whose effect is to improve the cosmetic properties of hair or the skin yet without adversely affecting the stability and/or washing and foaming properties of the compositions. In this context, non-limiting examples include cationic surfactants, anionic polymers, nonionic polymers, cationic polymers other than those of the invention, amphoteric polymers, proteins, protein hydrolysates, amino acids, ceramides, pseudoceramides, $C_{16}$–$C_{40}$ linear and branched-chain fatty acids such as 18-methyleicosanoic acid, hydroxy acids, vitamins, panthenol, fatty acid esters, silicones other than those of the invention, moisturizers, antidandruff and antiseborrhoeic agents, sunscreens, free-radical scavengers, mineral oils, vegetable oils, synthetic organic oils, and mixtures thereof.

The compositions of the invention may also comprise foam synergists such as $C_{10}$–$C_{18}$ 1,2-alkanediols, and fatty alkanolamides derived from mono- and diethanolamine.

The person skilled in the art will of course take care to select this or these optional additional compounds and/or the quantities thereof such that the advantageous properties associated intrinsically with the combination in accordance with the invention are not, or not substantially, adversely affected by the addition or additions envisaged.

The foaming power of the compositions according to the invention, characterized by a height of foam, is generally greater than 75 mm; in one embodiment the foam height is greater than 100 mm. Foam height is measured by the ROSS-MILES method (NF T 73-404/ISO696) with modifications.

The modifications of the method are as follows: The measurement is carried out at a temperature of 22° C. using osmosed water. The concentration of the solution is 2 g/l. The height of fall is 1 m. The amount of composition which falls is 200 ml. These 200 ml of composition fall into a test vessel having a diameter of 50 mm and containing 50 ml of the composition to be tested. The measurement is made 5 minutes after the composition has stopped flowing.

These compositions can be present in the form of more or less thickened liquids, creams or gels and are primarily suitable for the washing and care of hair.

When the compositions in accordance with the invention are employed as shampoos, they are simply applied to wetted hair and the foam generated by massage or rubbing with the hands is subsequently removed, possibly after a waiting time, by rinsing with water, it being possible for the operation to be repeated one or more times.

The invention additionally provides a method of washing and conditioning keratinous substances such as, in particular, the hair, which comprises applying an effective amount of a composition as defined above to the said substances, which have been wetted, and then in carrying out rinsing with water after an optional waiting period.

The compositions in accordance with the invention can also be used as shower gels, foam baths, foaming makeup removers, and for the washing and conditioning of the hair and/or skin, in which case they are applied to the wet hair and/or skin and are rinsed after application.

Specific but in no way limiting examples illustrating the invention will now be given.

EXAMPLE 1

Two shampoo compositions were made, one in accordance with the invention (composition A) and the other comparative (composition B): (a.s. signifies active substance):

|  | A (inventive) | B (comparative) |
|---|---|---|
| Sodium lauryl amido ether (3 EO) carboxylate as a solution containing 30% of a.s. in water (AKYPO FOAM 30 BV from KAO) | 14 g a.s. | — |
| Sodium $C_{12}$-$C_{14}$-alkyl ether sulphate ethoxylated with 2.2 mol of ethylene oxide, as an aqueous solution containing 70% of a.s. | — | 14 g a.s. |
| Hexadimethrine chloride in aqueous solution containing 60% a.s. (MEXOMER PO from CHIMEX) | 0.6 g a.s. | 0.6 g a.s. |
| Polydimethylsiloxane in aqueous nonionic emulsion containing 50% of a.s. (DC2-1691 from DOW CORNING) | 2.5 g a.s. | 2.5 g a.s. |
| Xanthan gum (KELTROL T from NUTRASWEET KELCO) | 1 g | 1 g |
| Preservatives | qs | qs |
| pH | pH 7 | pH 7 |
| Demineralized water qs for | 100 g | 100 g |

Shampooing was carried out by applying approximately 1 g of composition A to pre-wetted locks of 2.5 g of natural hair. The shampoo was foamed, a 10-minute waiting period was observed, and then the hair was rinsed with copious amounts of water.

The same procedure as above was followed for the comparative composition B.

A panel of experts evaluated the appearance of the wetted hair.

All of the experts indicated that the hair treated with composition A according to the invention was softer and disentangled more readily than that treated with composition B. The hair treated with composition A had a non-loaded feel.

EXAMPLE 2

Two shampoo compositions were made, one in accordance with the invention (composition A) and the other comparative (composition B): (a.s. signifies active substance):

|  | A (inventive) | B (comparative) |
|---|---|---|
| Sodium lauryl amido ether (3 EO) carboxylate as a solution containing 30% of a.s. in water (AKYPO FOAM 30 BV from KAO) | 10 g a.s. | — |
| Sodium $C_{12}$-$C_{14}$-alkyl ether sulphate ethoxylated with 2.2 mol of ethylene oxide, as an aqueous solution containing 70% of a.s. | 4 g a.s. | 14 g a.s. |
| Hexadimethrine chloride in aqueous solution containing 60% a.s. (MEXOMER PO from CHIMEX) | 0.6 g a.s. | 0.6 g a.s. |
| Polydimethylsiloxane in aqueous nonionic emulsion containing 50% of a.s. (DC2-1691 from DOW CORNING) | 2.5 g a.s. | 2.5 g a.s. |
| Xanthan gum (KELTROL T from NUTRASWEET KELCO) | 1 g | 1 g |
| Preservatives | qs | qs |
| pH | pH 7 | pH 7 |
| Demineralized water qs for | 100 g | 100 g |

Shampooing was carried out by applying approximately 1 g of composition A to pre-wetted locks of 2.5 g of natural hair. The shampoo was foamed, a 10-minute waiting period was observed, and then the hair was rinsed with copious amounts of water.

The same procedure as above was followed for the comparative composition B.

A panel of experts evaluated the appearance of the wetted hair.

All of the experts indicated that the hair treated with composition A according to the invention was softer and disentangled more readily than that treated with composition B. The hair treated with composition A had a non-loaded feel.

EXAMPLE 3

Two shampoo compositions were made, one in accordance with the invention (composition A) and the other comparative (composition B): (a.s. signifies active substance):

|  | A (Invention) | B (Ex. 10 of U.S. Pat. No. 5,180,584) |
|---|---|---|
| Ethoxylated (7 EO) nonylphenol ether carboxylic acid (AKYPO NP 70 from CHEM Y) | 7.2 g a.s. | 7.2 g a.s. |
| Triethanolamine $C_{12}$-$C_{14}$ alkyl sulphate in aqueous solution containing 40% a.s. | 10 g a.s. | 10 g a.s. |
| Sodium laurylsarcosinate in aqueous solution containing 30% of a.s. (ORAMIX L30 from SEPPIC) | 4 g a.s. | 4 g a.s. |
| Hexadimethrine chloride in aqueous solution containing 60% a.s. (MEXOMER PO from CHIMEX) | 1 g a.s. | — |
| Silicone oil (Huile 70633 V 30 from RHONE POULENC) | 2 g | 2 g |
| Dimethicone copolyol (Huile CL 183/25 from GOLDSCHMIDT) | 5 g a.s. | 5 g a.s. |
| Hydroxyethylcellulose crosslinked with epichlorohydrin and quaternized with triethanolamine (JR 400 from UNION CARBIDE) | — | 1 g a.s. |
| Triethanolamine qs |  |  |
| pH | pH 6 | pH 6 |
| Demineralized water qs for | 100 g | 100 g |

Shampooing was carried out by applying approximately 1 g of composition A to pre-wetted locks of 2.5 g of natural hair. The shampoo was foamed, a 10-minute waiting period was observed, and then the hair was rinsed with copious amounts of water.

The same procedure as above was followed for the comparative composition B.

A panel of experts evaluated the appearance of the wetted hair. 90% of the experts indicated that the hair treated with composition A according to the invention was softer and smoother and disentangled more readily than that treated with composition B.

The hair treated with composition A had a non-loaded feel.

EXAMPLE 4

Two shampoo compositions were made, one in accordance with the invention (composition A) and the other comparative (composition B): (a.s. signifies active substance):

|  | A (Invention) | B (Ex. 17 of U.S. Pat. No. 5,180,584) |
|---|---|---|
| Ethoxylated (7 EO) nonylphenol ether carboxylic acid (AKYPO NP 70 from CHEM Y) | 4.5 g a.s. | 4.5 g a.s. |
| Sodium $C_{12}$-$C_{14}$ alkyl sulphate in aqueous solution containing 40% a.s. | 10 g a.s. | 10 g a.s. |
| Lauryl betaine in aqueous solution containing 30% of a.s. (DEHYTON AB 30 from HENKEL) | 5 g a.s. | 5 g a.s. |
| Hexadimethrine chloride in aqueous solution containing 60% a.s. (MEXOMER PO from CHIMEX) | 0.5 g a.s. | — |
| Quaternized protein in aqueous solution containing 30% of a.s. (LEXEIN QX 3000 from INOLEX) | — | 0.5 g a.s. |
| Silicone resin (DC 593 from DOW CORNING) | 0.5 g a.s. | 0.5 g a.s. |
| Stearyldimethylbenzylammonium chloride | 1 g | 1 g |
| Spontaneous pH | 3.6 | 3.6 |
| Demineralized water qs for | 100 g | 100 g |

Shampooing was carried out by applying approximately 1 g of composition A to pre-wetted locks of 2.5 g of natural hair. The shampoo was foamed, a 10-minute waiting period was observed, and then the hair was rinsed with copious amounts of water.

The same procedure as above was followed for the comparative composition B.

A panel of experts evaluated the appearance of the wetted hair. 90% of the experts indicated that the hair treated with composition A according to the invention was softer and smoother and disentangled more readily than that treated with composition B.

The hair treated with composition A had a non-loaded feel.

What is claimed is:

1. A cosmetic conditioning and detergent composition comprising:

(A) at least one anionic surfactant derived from a carboxylic acid, wherein said at least one anionic surfactant does not include a sulphate or sulphonate function and wherein said at least one anionic surfactant is present in an amount ranging from 3 to 50% by weight, relative to the total weight of the composition;

(B) at least one silicone which does not include an amide function, which is present in a conditioning amount; and (C) at least one cationic polymer, which contains quaternary ammonium groups in the polymeric main chain, chosen from:

(1) quaternary diammonium polymers containing repeating units of the formula:

wherein $R_1$, $R_2$, $R_3$, and $R_4$, which are identical or different, are chosen from aliphatic, alicyclic, and arylaliphatic radicals containing 1 to 20 carbon atoms or lower hydroxyalkyl aliphatic radicals; or else $R_1$, $R_2$, $R_3$, and R4, together or separately, together with the nitrogen atoms to which they are attached, form heterocycles optionally containing a second heteroatom other than nitrogen; or else $R_1$, $R_2$, $R_3$, and $R_4$ are chosen from linear and branched $C_1$–$C_6$ alkyl radicals substituted by a group chosen from nitrile, ester, acyl, amide, —CO—O—$R_5$—D, and —CO—NH—$R_5$—D, wherein $R_5$ is chosen from alkylenes and D is chosen from quaternary ammonium groups;

$A_1$ and $B_1$ are chosen from linear and branched, saturated and unsaturated polymethylene groups which contain 2 to 20 carbon atoms, and which can contain, bonded to or intercalated in the polymeric main chain, at least one aromatic ring or at least one group chosen from an oxygen atom, a sulfur atom, and sulphoxide, sulphone, disulphide, amino, alkylamino, hydroxyl, quaternary ammonium, ureido, amide, and ester groups, $X^-$ is chosen from anions derived from a mineral or organic acid;

$A_1$, $R_1$ and $R_3$ can, together with the two nitrogen atoms to which they are attached, form a piperazine ring; and, if $A_1$ is a linear or branched, saturated or unsaturated alkylene or hydroxyalkylene radical, $B_1$ may also be a group $(CH_2)_n$—CO—D—OC—$(CH_2)_n$— in which D is chosen from:

a) a glycol residue of formula —O—Z—O—, in which Z is chosen from linear and branched hydrocarbon radicals, —$(CH_2$—$CH_2$—$O)_x$—$CH_2$—$CH_2$—, and —$(CH_2$—$CH(CH_3)$—$O)_y$—$CH_2$—$CH(CH_3)$— in which x and y are chosen from integers from 1 to 4, representing a defined and single degree of polymerization, and any number from 1 to 4, representing an average degree of polymerization;

b) a bis-secondary diamine residue;

c) a bis-primary diamine residue of formula —NH—Y—NH—, in which Y is chosen from linear and branched hydrocarbon radicals and the divalent radical —$CH_2$—$CH_2$—S—S—$CH_2$—$CH_2$—;

d) a ureylene group of formula —NH—CO—NH—, (2) quaternary polyammonium polymers comprising of units of formula (II):

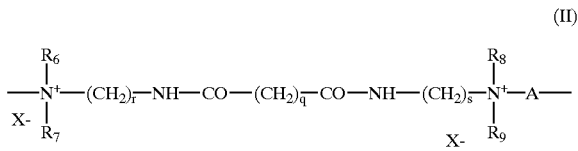

(II)

wherein $R_6$, $R_7$, $R_8$ and $R_9$, which are identical or different, are chosen from a hydrogen atom, a methyl, ethyl, propyl, β-hydroxyethyl, β-hydroxypropyl, and —$CH_2CH_2(OCH_2CH_2)_p$OH radical,
in which p is an integer ranging from 0 to 6, with the proviso that $R_6$, $R_7$, $R_8$ and $R_9$ are not simultaneously a hydrogen atom,
r and s, which are identical or different, are integers ranging from 1 to
q is an integer ranging from 0 to 34,
X is chosen from halogen atoms,
A is a radical of a dihalide or —$CH_2$—$CH_2$—O—$CH_2$—$CH_2$—, (3) polymers comprising piperazinyl units and radicals chosen from divalent straight-chain and branched hydroxyalkylene and alkylene radicals, optionally interrupted by oxygen, sulphur or nitrogen atoms or by aromatic or heterocyclic rings, and the oxidation and/or quaternization products of these polymers, (4) water-soluble polyaminoamides, (5) polyaminoamide derivatives resulting from the condensation of polyalkylene polyamines with polycarboxylic acids followed by alkylation with bifunctional agents, (6) polymers obtained by reacting a polyalkylene polyamine containing two primary amine groups and at least one secondary amine group with a dicarboxylic acid chosen from diglycolic acid and saturated aliphatic dicarboxylic acids having 3 to 8 carbon atoms, wherein the molar ratio of polyalkylene polyamine to dicarboxylic acid ranges from 0.8:1 to 1.4:1; the resulting polyaminoamide being reacted with epichlorohydrin in a molar ratio ranging from 0.5:1 to 1.8:1 of epichlorohydrin relative to the secondary amine group of the polyaminoamide, (7) alkyldiallylamine and dialkyldiallylammonium cyclic polymers, and (8) quaternary polymers of vinylpyrrolidone and vinylimidazolium.

2. A composition according to claim 1, wherein said at least one anionic surfactant derived from a carboxylic acid is chosen from alkyl-D-galactoside-uronic acids and their salts, polyalkoxylated $C_6$–$C_{24}$-alkyl ether carboxylic acids, polyalkoxylated ($C_6$–$C_{24}$-alkyl)aryl ether carboxylic acids, polyalkoxylated $C_6$–$C_{24}$-alkylamido ether carboxylic acids and their salts, ($C_6$–$C_{24}$-acyl)sarcosinates, ($C_6$–$C_{24}$-acyl)glutamates, and ($C_6$–$C_{24}$-alkyl)polyglycoside carboxylic esters.

3. A composition according to claim 2, wherein the polyalkoxylated $C_6$–$C_{24}$-alkylamido ether carboxylic acids and their salts are chosen from those containing from 2 to 50 alkylene oxide groups.

4. A composition according to claim 3, wherein the alkylene oxide groups are chosen from ethylene oxide groups.

5. A composition according to claim 2, wherein said at least one anionic surfactant derived from a carboxylic acid is chosen from polyalkoxylated $C_6$–$C_{24}$-alkyl ether carboxylic acids, polyalkoxylated $C_6$–$C_{24}$-alkylamido ether carboxylic acids, and ($C_6$–$C_{24}$-alkyl)polyglycoside carboxylic esters.

6. A composition according to claim 5, wherein the polyalkoxylated $C_6$–$C_{24}$-alkylamido ether carboxylic acids are chosen from those containing from 2 to 15 alkylene oxide groups.

7. A composition according to claim 1, where the at least one silicone is chosen from:

(i) polyalkylsiloxanes;

(ii) polyarylsiloxanes;

(iii) polyalkylarylsiloxanes;

(iv) silicone gums;

(v) silicone resins;

(vi) polyorganosiloxanes comprising in their structure at least one organic functional group attached directly to the siloxane chain or attached via a hydrocarbon radical;

(vii) block copolymers having a linear polysiloxane-polyoxyalkylene block as repeating units;

(viii) graft silicone polymers, having a non-silicone organic framework, which comprise an organic main chain which is formed from non-silicone organic monomers and onto which there is grafted, within said chain and optionally at at least one of its ends, at least one polysiloxane macromonomer; and (ix) graft silicone polymers, having a polysiloxane framework grafted with non-silicone organic monomers, which comprise a polysiloxane main chain to which there is grafted, within said chain and optionally at at least one of its ends, at least one non-silicone organic macromonomer.

8. A composition according to claim 1, wherein the bis-secondary diamine residue is chosen from piperazine derivatives.

9. A composition according to claim 1, wherein in said units of formula (II), A is a —$CH_2$—$CH_2$—O—$CH_2$—$CH_2$— radical.

10. A composition according to claim 1, wherein the water-soluble polyaminoamides are prepared by polycondensation of an acid compound with a polyamine.

11. A composition according to claim 1, wherein the water-soluble polyaminoamides are prepared by polycondensation of an acid compound with a polyamine and may be crosslinked by a compound chosen from: epihalohydrins, diepoxides, dianhydrides, unsaturated anhydrides, diunsaturated derivatives, bishalohydrins, bisazetidimiums, bishaloacyidiamines, bisalkyl halides; and oligomers resulting from the reaction of a bifunctional compound which is reactive with respect to a compound chosen from bishalohydrins, bisazetidinium, bishaloacyldiamine, bisalkyl halides, epihalohydrins, diepoxides, and diunsaturated derivatives, wherein the crosslinking agent is present in an amount ranging from 0.025 to 0.35 mol per amine group of the polyaminoamide.

12. A composition according to claim 1, wherein the alkyldiallylamine and dialkyldiallylammonium cyclic polymers are chosen from the homopolymers and copolymers containing, as principal constituent of the chain, units corresponding to the formulae (VI) or (VI'):

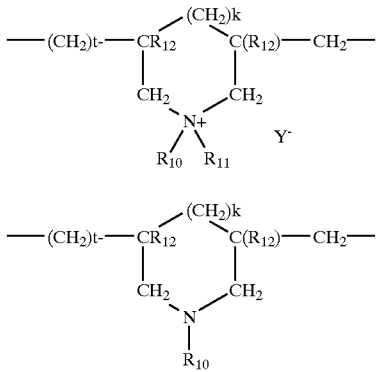

in which k and t are 0 or 1, and the sum k+t is equal to 1; $R_{12}$ is chosen from a hydrogen atom and a methyl radical; $R_{10}$ and $R_{11}$, which can be identical or different, are chosen from alkyl groups having 1 to 22 carbon atoms, hydroxyalkyl groups, lower ($C_1$–$C_4$) amidoalkyl groups; or, in formula (VI), $R_{10}$ and $R_{11}$, in conjunction with the nitrogen atom to which they are attached, form a heterocyclic group, and, in formula (VI'), $R_{10}$, in conjunction with the nitrogen atom to which it is attached, forms a heterocyclic group; and $Y^-$ is an anion.

13. A composition according to claim 12, wherein the hydroxylkyl group is chosen from hydroxyalkyl groups in which the alkyl group has from 1 to 5 carbon atoms.

14. A composition according to claim 12, wherein the heterocyclic groups are chosen from piperidinyl and morpholinyl groups.

15. A composition according to claim 12, wherein the anion $Y^-$ is chosen from bromide, chloride, acetate, borate, citrate, tartrate, bisulphate, bisulphite, sulphate, and phosphate anions.

16. A composition according to claim 1, wherein said at least one cationic polymer is chosen from polymers which comprise repeating units corresponding to the formula:

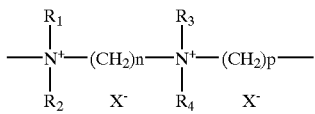
(a)

in which $R_1$, $R_2$, $R_3$ and R4, which are identical or different, are chosen from alkyl and hydroxyalkyl radicals having 1 to 4 carbon atoms, n and p are integers ranging from 2 to 20, and $X^-$ is chosen from anions derived from mineral or organic acids.

17. A composition according to claim 1, wherein said at least one cationic polymer is chosen from diallyldimethylammonium chloride homopolymers and diallyldimethylammonium chloride-acrylamide copolymers.

18. A composition according to claim 1, further comprising at least one additional surfactant, wherein said at least one additional surfactant is chosen from anionic surfactants derived from phosphate, sulphonate and sulphate, amphoteric surfactants, nonionic surfactants, and cationic surfactants.

19. A composition according to claim 1, wherein said at least one silicone is present in an amount ranging from 0.05% to 10% by weight, relative to the total weight of the composition.

20. A composition according to claim 19, wherein said at least one silicone is present in an amount ranging from 0.1% to 5% by weight, relative to the total weight of the composition.

21. A composition according to claim 20, wherein said at least one silicone is present in an amount ranging from 0.5% to 3% by weight, relative to the total weight of the composition.

22. A composition according to claim 1, wherein the amount ranging from 3 to 20% by weight, relative to the total weight of the composition.

23. A composition according to any claim 1, wherein said at least one cationic polymer is present in an amount ranging from 0.005% to 10% by weight, relative to the total weight of the composition.

24. A composition according to claim 23, wherein said at least one cationic polymer is present in an amount ranging from 0.01% to 5% by weight, relative to the total weight of the composition.

25. A composition according to claim 24, wherein said at least one cationic polymer is present in an amount ranging from 0.1% to 3% by weight, relative to the total weight of the composition.

26. A composition according to claim 18, wherein the total amount of said at least one anionic surfactant derived from a carboxylic acid and said at least one additional surfactant ranges from 3 to 50% by weight relative to the total weight of the composition.

27. A composition according to claim 1, further comprising at least one adjuvant chosen from cationic surfactants, anionic polymers, nonionic polymers, cationic polymers that do not contain a quaternary ammonium group in their polymeric main chain, amphoteric polymers, proteins, protein hydrolysates, amino acids, ceramides, pseudoceramides, hydroxy acids, vitamins, panthenol, moisturizers, antidandruff and antiseborrhoeic agents, sunscreens, and free-radical scavengers.

28. A composition for the simultaneous care and washing of keratinous substances comprising:

(A) at least one anionic surfactant derived from a carboxylic acid, wherein said at least one anionic surfactant does not include a sulphate or sulphonate function and wherein said at least one anionic surfactant is present in an amount ranging from 3 to 50% by weight, relative to the total weight of the composition;

(B) at least one silicone which does not include an amide function, which is present in a conditioning amount; and (C) at least one cationic polymer, which contains quaternary ammonium. groups in the polymeric main chain, chosen from:

(1) quaternary diammonium polymers containing repeating units of the formula:

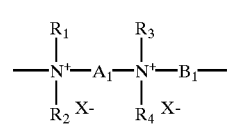
(I)

wherein $R_1$, $R_2$, $R_3$, and R4, which are identical or different, are chosen from aliphatic, alicyclic, and arylaliphatic radicals containing 1 to 20 carbon atoms or lower hydroxyalkyl aliphatic radicals; or else $R_1$, $R_2$, $R_3$, and $R_4$, together or separately, together with the nitrogen atoms to which they are attached, form heterocycles optionally containing a second heteroatom other than nitrogen; or else $R_1$, $R_2$, $R_3$, and $R_4$ are chosen from linear and branched $C_1$–$C_6$ alkyl radicals substituted by a group chosen from nitrile, ester, acyl, amide, —CO—O—R$_5$—D, and —CO—NH—R$_5$—D, wherein R$_5$ is chosen from alkylenes and D is chosen from quaternary ammonium groups;

A$_1$ and B$_1$ are chosen from linear and branched, saturated and unsaturated polymethylene groups which contain 2 to 20 carbon atoms, and which can contain, bonded to or intercalated in the polymeric main chain, at least one aromatic ring or at least one group chosen from an oxygen atom, a sulfur atom, and sulphoxide, sulphone, disulphide, amino, alkylamino, hydroxyl, quaternary ammonium, ureido, amide, and ester groups, X$^-$ is chosen from anions derived from a mineral or organic acid;

A$_1$, R$_1$ and R$_3$ can, together with the two nitrogen atoms to which they are attached, form a piperazine ring; and, if A$_1$ is a linear or branched, saturated or unsaturated alkylene or hydroxyalkylene radical, B$_1$ may also be a group (CH$_2$)$_n$—CO—D—OC—(CH$_2$)$_n$— in which D is chosen from:

a) a glycol residue of formula —O—Z—O—, in which Z is chosen from linear and branched hydrocarbon radicals,

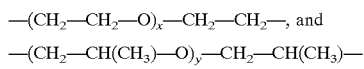

in which x and y are chosen from integers from 1 to 4, representing a defined and single degree of polymerization, and any number from 1 to 4, representing an average degree of polymerization;

b) a bis-secondary diamine residue;

c) a bis-primary diamine residue of formula —NH—Y—NH—, in which Y is chosen from linear and branched hydrocarbon radicals and the divalent radical —CH$_2$—CH$_2$—S—S—CH$_2$—CH$_2$—;

d) a ureylene group of formula —NH—CO—NH—, (2) quaternary polyammonium polymers comprising of units of formula (II):

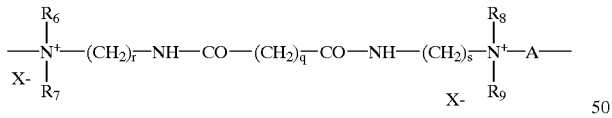

wherein R$_6$, R$_7$, R$_8$ and R$_9$, which are identical or different, are chosen from a hydrogen atom, a methyl, ethyl, propyl, β-hydroxyethyl, β-hydroxypropyl, and —CH$_2$CH$_2$(OCH$_2$CH$_2$)$_p$OH radical, in which p is an integer ranging from 0 to 6, with the proviso that R$_6$, R$_7$, R$_8$ and R$_9$ are not simultaneously a hydrogen atom, r and s, which are identical or different, are integers ranging from 1 to q is an integer ranging from 0 to 34, X is chosen from halogen atoms, A is a radical of a dihalide or —CH$_2$—CH$_2$—O—CH$_2$—CH$_2$—, (3) polymers comprising piperazinyl units and radicals chosen from divalent straight-chain and branched hydroxyalkylene and alkylene radicals, optionally interrupted by oxygen, sulphur or nitrogen atoms or by aromatic or heterocyclic rings, and the oxidation and/or quaternization products of these polymers, (4) water-soluble polyaminoamides, (5) polyaminoamide derivatives resulting from the condensation of polyalkylene polyamines with polycarboxylic acids followed by alkylation with bifunctional agents, (6) polymers obtained by reacting a polyalkylene polyamine containing two primary amine groups and at least one secondary amine group with a dicarboxylic acid chosen from diglycolic acid and saturated aliphatic dicarboxylic acids having 3 to 8 carbon atoms, wherein the molar ratio of polyalkylene polyamine to dicarboxylic acid ranges from 0.8:1 to 1.4:1; the resulting polyaminoamide being reacted with epichlorohydrin in a molar ratio ranging from 0.5:1 to 1.8:1 of epichlorohydrin relative to the secondary amine group of the polyaminoamide, (7) alkyldiallylamine and dialkyldiallylammonium cyclic polymers, (8) quaternary polymers of vinylpyrrolidone and vinylimidazolium.

29. A process for washing and conditioning keratinous substances, comprising:

applying an effective amount of a composition to wetted keratinous substances, and then rinsing said keratinous substances with water after an optional waiting period, wherein said composition comprises:

(A) at least one anionic surfactant derived from a carboxylic acid, wherein said at least one anionic surfactant does not include a sulphate or sulphonate function and wherein said at least one anionic surfactant is present in an amount ranging from 3 to 50% by weight, relative to the total weight of the composition;

(B) at least one silicone which does not include an amide function, which is present in a conditioning amount; and (C) at least one cationic polymer, which contains quaternary ammonium groups in the polymeric main chain, chosen from:

(1) quaternary diammonium polymers containing repeating units of the formula:

wherein R$_1$, R$_2$, R$_3$, and R$_4$, which are identical or different, are chosen from aliphatic, alicyclic, and arylaliphatic radicals containing 1 to 20 carbon atoms or lower hydroxyalkyl aliphatic radicals; or else R$_1$, R$_2$, R$_3$, and R$_4$, together or separately, together with the nitrogen atoms to which they are attached, form heterocycles optionally containing a second heteroatom other than nitrogen; or else R$_1$, R$_2$, R$_3$, and R$_4$ are chosen from linear and branched C$_1$–C$_6$ alkyl radicals substituted by a group chosen from nitrile, ester, acyl, amide, —CO—O—R$_5$—D, and CO—NH—R$_5$—D, wherein R$_5$ is chosen from alkylenes and D is chosen from quaternary ammonium groups;

A₁ and B₁ are chosen from linear and branched, saturated and unsaturated polymethylene groups which contain 2 to 20 carbon atoms, and which can contain, bonded to or intercalated in the polymeric main chain, at least one aromatic ring or at least one group chosen from an oxygen atom, a sulfur atom, and sulphoxide, sulphone, disulphide, amino, alkylamino, hydroxyl, quaternary ammonium, ureido, amide, and ester groups, X⁻ is chosen from anions derived from a mineral or organic acid;

A₁, R₁ and R₃ can, together with the two nitrogen atoms to which they are attached, form a piperazine ring; and, if A₁ is a linear or branched, saturated or unsaturated alkylene or hydroxyalkylene radical, B₁ may also be a group $(CH_2)_n$—CO—D—OC—$(CH_2)_n$— in which D is chosen from:
  a) a glycol residue of formula —O—Z—O—, in which Z is chosen from linear and branched hydrocarbon radicals, —(CH₂—CH₂—O)ₓ—CH₂—CH₂—, and

—(CH₂—CH(CH₃)—O)ᵧ—CH₂—CH(CH₃)— in which x and y are chosen from integers from 1 to 4, representing a defined and single degree of polymerization, and any number from 1 to 4, representing an average degree of polymerization;

b) a bis-secondary diamine residue;
  c) a bis-primary diamine residue of formula —NH—Y—NH—, in which Y is chosen from linear and branched hydrocarbon radicals and the divalent radical —CH₂—CH₂—S—S—CH₂—CH₂—,
  d) a ureylene group of formula —NH—CO—NH—, (2) quaternary polyammonium polymers comprising of units of formula (II):

(II)

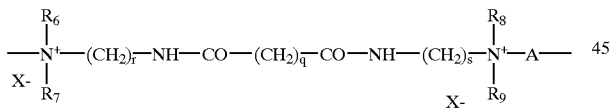

wherein R₆, R₇, R₈ and R₉, which are identical or different, are chosen from a hydrogen atom, a methyl, ethyl, propyl, β-hydroxyethyl, β-hydroxypropyl, and —CH₂CH₂(OCH₂CH₂)ₚOH radical, in which p is an integer ranging from 0 to 6, with the proviso that R₆, R₇, R₈ and R₉ are not simultaneously a hydrogen atom, r and s, which are identical or different, are integers ranging from 1 to q is an integer ranging from 0 to 34, X is chosen from halogen atoms, A is a radical of a dihalide or —CH₂—CH₂—O—CH₂—CH₂—, (3) polymers comprising piperazinyl units and radicals chosen from divalent straight-chain and branched hydroxyalkylene and alkylene radicals, optionally interrupted by oxygen, sulphur or nitrogen atoms or by aromatic or heterocyclic rings, and the oxidation and/or quaternization products of these polymers, (4) water-soluble polyaminoamides, (5) polyaminoamide derivatives resulting from the condensation of polyalkylene polyamines with polycarboxylic acids followed by alkylation with bifunctional agents, (6) polymers obtained by reacting a polyalkylene polyamine containing two primary amine groups and at least one secondary amine group with a dicarboxylic acid chosen from diglycolic acid and saturated aliphatic dicarboxylic acids having 3 to 8 carbon atoms, wherein the molar ratio of polyalkylene polyamine to dicarboxylic acid ranges from 0.8:1 to 1.4:1; the resulting polyaminoamide being reacted with epichlorohydrin in a molar ratio ranging from 0.5:1 to 1.8:1 of epichlorohydrin relative to the secondary amine group of the polyaminoamide, (7) alkyldiallylamine and dialkyldiallylammonium cyclic polymers, and (8) quaternary polymers of vinylpyrrolidone and vinylimidazolium.

* * * * *

UNITED STATES PATENT AND TRADEMARK OFFICE
CERTIFICATE OF CORRECTION

PATENT NO. : 6,410,493 B1
DATED : June 25, 2002
INVENTOR(S) : Nathalie Garnier

It is certified that error appears in the above-identified patent and that said Letters Patent is hereby corrected as shown below:

Column 19,
Line 20, after "1 to" insert -- 6 --;
Lines 56 and 57, "g lutamates" should read -- glutamates --.

Column 20,
Line 54, "bishaloacyidiamines" should read -- bishaloacyldiamines --;

Column 21,
Line 26, "Y⁻ is ananion" should read -- Y⁻ is an anion --;
Line 28, "hydroxylkyl" should read -- hydroxyalkyl --;
Line 46, "R4" should read -- $R_4$ --;

Column 22,
Line 5, after "wherein the" insert -- at least on anionic surfactant derived from a carboxylic acid is present in an --;
Line 8, before "claim 1" delete "any";
Line 28, "quatemary" should read -- quaternary --;
Line 47, after "ammonium" delete the period;
Line 58, "R4" should read -- $R_4$ --;

Column 23,
Line 61, after "1 to " insert -- 6, --;

Column 24,
Line 21, after "polymers," insert -- and --;

Column 25,
Line 8, "quatemary" should read -- quaternary --;
Line 39, "quatemary" should read -- quaternary --;

UNITED STATES PATENT AND TRADEMARK OFFICE
CERTIFICATE OF CORRECTION

PATENT NO. : 6,410,493 B1
DATED : June 25, 2002
INVENTOR(S) : Nathalie Garnier

It is certified that error appears in the above-identified patent and that said Letters Patent is hereby corrected as shown below:

Column 26,
Line 11, after "1 to" insert -- 6, --; and
Line 13, "chose n" should read -- chosen --.

Signed and Sealed this

Twenty-fourth Day of September, 2002

Attest:

Attesting Officer

JAMES E. ROGAN
*Director of the United States Patent and Trademark Office*